United States Patent
Justis et al.

(10) Patent No.: US 8,945,187 B2
(45) Date of Patent: Feb. 3, 2015

(54) SPINAL RODS HAVING DIFFERENT FLEXURAL RIGIDITIES ABOUT DIFFERENT AXES AND METHODS OF USE

(75) Inventors: Jeff R. Justis, Germantown, TN (US); Fred J. Molz, IV, Birmingham, AL (US); Michael C. Sherman, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 761 days.

(21) Appl. No.: 13/181,474

(22) Filed: Jul. 12, 2011

(65) Prior Publication Data
US 2011/0270313 A1 Nov. 3, 2011

Related U.S. Application Data

(62) Division of application No. 11/342,195, filed on Jan. 27, 2006, now abandoned.

(51) Int. Cl.
*A61B 17/70* (2006.01)

(52) U.S. Cl.
CPC ......... *A61B 17/7029* (2013.01); *A61B 17/7002* (2013.01); *A61B 17/701* (2013.01)

USPC ............ 606/254; 606/261; 606/265; 606/257

(58) Field of Classification Search
CPC ......................... A61B 17/7029; A61B 17/701
USPC .......................... 606/254, 255, 257, 261, 262
See application file for complete search history.

(56) References Cited

U.S. PATENT DOCUMENTS

| | | | | |
|---|---|---|---|---|
| 6,102,912 A | * | 8/2000 | Cazin et al. | 606/86 A |
| 7,326,210 B2 | * | 2/2008 | Jahng et al. | 606/86 A |
| 7,563,274 B2 | * | 7/2009 | Justis et al. | 606/279 |
| 2003/0220642 A1 | * | 11/2003 | Freudiger | 606/61 |
| 2004/0215191 A1 | * | 10/2004 | Kitchen | 606/61 |
| 2006/0149228 A1 | * | 7/2006 | Schlapfer et al. | 606/61 |

* cited by examiner

Primary Examiner — Ellen C Hammond

(57) ABSTRACT

A vertebral rod for stabilizing a patient's spine. The rod may include an elongated body with first and second ends and have an elongated cross-sectional shape with a major axis and a minor axis and a centroid positioned at an intersection of the axes. First and second longitudinal channels may extend through the body. The channels may be spaced apart and contained within the body. The body may have a first flexural rigidity along the major axis and a different second flexural rigidity along the minor axis.

18 Claims, 4 Drawing Sheets

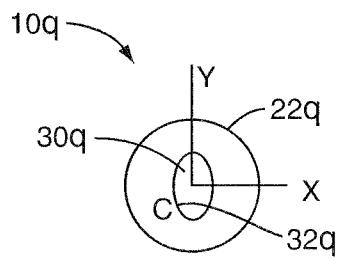
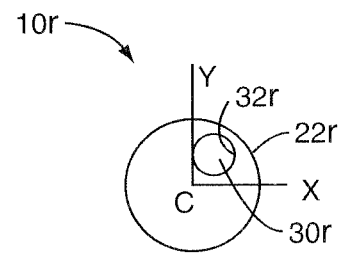
FIG. 17                FIG. 18
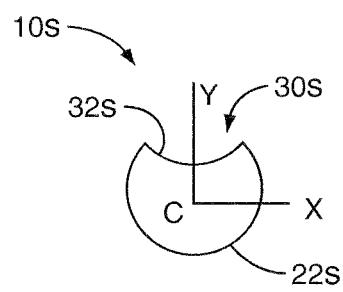
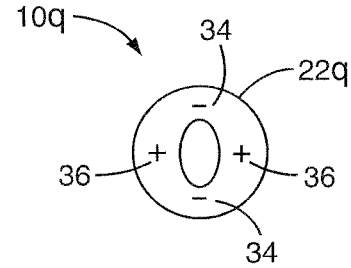
FIG. 19                FIG. 20

SPINAL RODS HAVING DIFFERENT FLEXURAL RIGIDITIES ABOUT DIFFERENT AXES AND METHODS OF USE

RELATED APPLICATION

The present application is a divisional application of U.S. patent application Ser. No. 11/342,195 filed on Jan. 27, 2006, now abandoned, which is herein incorporated by reference in its entirety.

BACKGROUND

Spinal or vertebral rods are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral bodies. In other cases, dynamic implants are used to preserve motion between vertebral bodies. For either type of surgical treatment, spinal rods may be attached to the exterior of two or more vertebrae, whether it is at a posterior, anterior, or lateral side of the vertebrae. In other embodiments, spinal rods are attached to the vertebrae without the use of dynamic implants or spinal fusion.

Spinal rods may provide a stable, rigid column that encourages bones to fuse after spinal-fusion surgery. Further, the rods may redirect stresses over a wider area away from a damaged or defective region. Also, a rigid rod may restore the spine to its proper alignment. In some cases, a flexible rod may be appropriate. Flexible rods may provide some advantages over rigid rods, such as increasing loading on interbody constructs, decreasing stress transfer to adjacent vertebral elements while bone-graft healing takes place, and generally balancing strength with flexibility.

Aside from each of these characteristic features, a surgeon may wish to control anatomic motion after surgery. That is, a surgeon may wish to inhibit or limit one type of spinal motion following surgery while allowing a lesser or greater degree of motion in a second direction. As an illustrative example, a surgeon may wish to inhibit or limit motion in the flexion and extension directions while allowing for a greater degree of lateral bending. However, conventional rods tend to be symmetric in nature and may not provide this degree of control.

SUMMARY

The present application is directed to vertebral rods for stabilizing a patient's spine. One rod includes a solid elongated body with first and second ends. The rod has an elongated cross-sectional shape with a major axis and a minor axis and a centroid positioned at an intersection of the axes. First and second longitudinal channels extend through the body. The channels are spaced apart and are each contained within the body. Each of the channels is positioned on the major axis and is spaced away from the centroid. The body is limited to just the first and second longitudinal channels with a remainder of the body being channel-free. The body has a first flexural rigidity along the major axis and a different second flexural rigidity along the minor axis.

Another rod includes an elongated body with an elliptical cross-sectional shape having a major axis and a minor axis. The body consists of first and second longitudinal channels that extend along a length of the body. The channels are being positioned on and spaced apart along the major axis and contained within an interior of the body. The body has a first flexural rigidity along the major axis and a different second flexural rigidity along the minor axis.

Another rod includes an elongated body with first and second ends and an elliptical cross-sectional shape with perpendicular major and minor axes. A centroid is positioned at an intersection of the axes. First and second longitudinal channels extend through the body. The channels have circular cross-sectional shapes and are spaced apart on the major axis. The channels are contained within the body and are spaced away from the centroid. The body is limited to just the first and second longitudinal channels. The body has a first flexural rigidity along the major axis and a different second flexural rigidity along the minor axis.

BRIEF DESCRIPTION OF THE DRAWINGS

FIGS. 3-20 are axial views of a spinal rod illustrating cross sections according to different embodiments.

DETAILED DESCRIPTION

Figure 1:
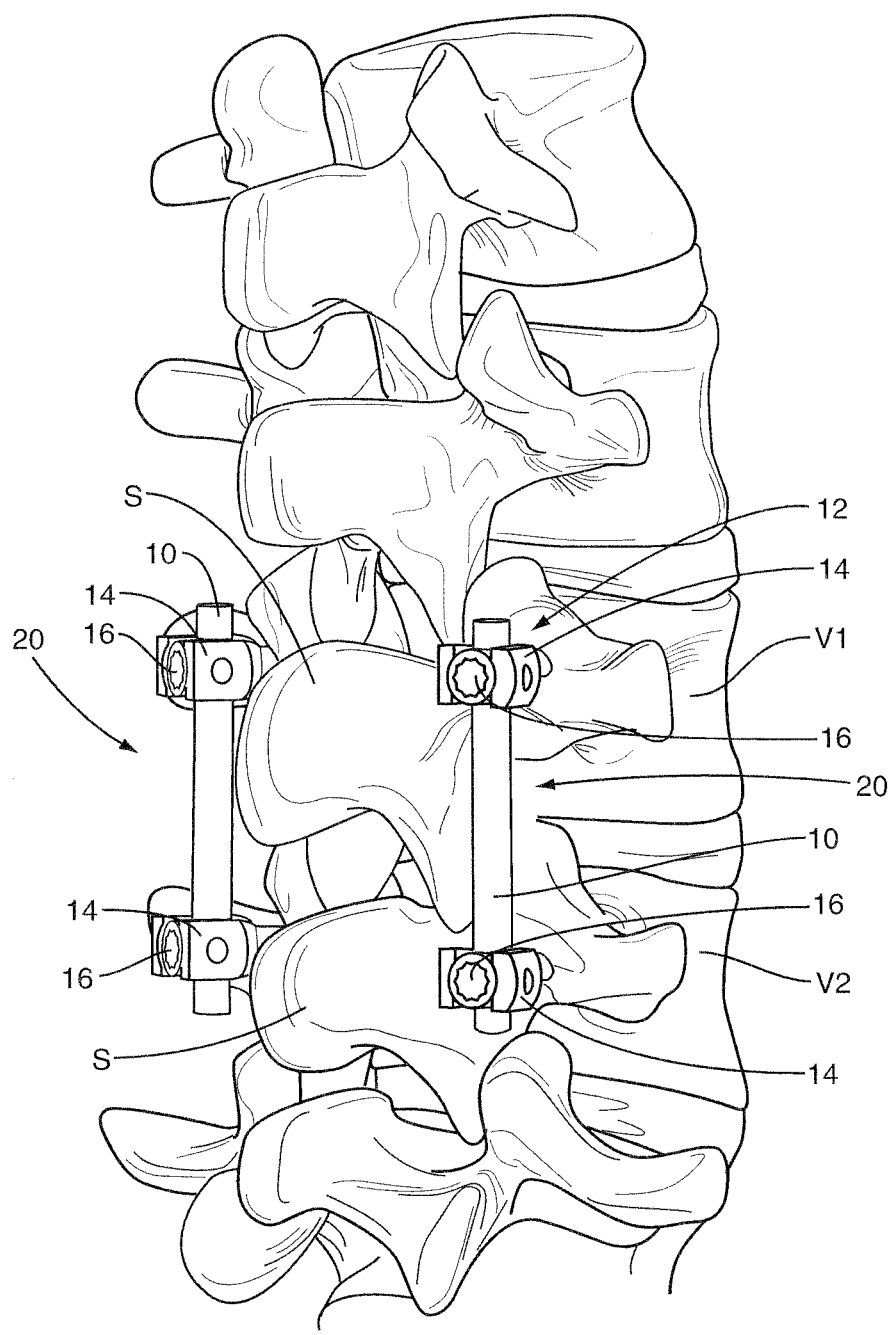
FIG. 1 is a perspective view of first and second assemblies comprising spinal rods attached to vertebral members according to one or more embodiments.

The various embodiments disclosed herein are directed to spinal rods that are characterized by a cross section that provides different flexural rigidities in different directions. Various embodiments of a spinal rod may be implemented in a spinal rod assembly of the type indicated generally by the numeral 20 in FIG. 1. FIG. 1 shows a perspective view of first and second spinal rod assemblies 20 in which spinal rods 10 are attached to vertebral members V1 and V2. In the example assembly 20 shown, the rods 10 are positioned at a posterior side of the spine, on opposite sides of the spinous processes S. Spinal rods 10 may be attached to a spine at other locations, including lateral and anterior locations. Spinal rods 10 may also be attached at various sections of the spine, including the base of the skull and to vertebrae in the cervical, thoracic, lumbar, and sacral regions. In one embodiment, a single rod 10 is attached to the spine. Thus, the illustration in FIG. 1 is provided merely as a representative example of one application of a spinal rod 10.

In one embodiment as illustrated in FIG. 1, the spinal rods 10 are secured to vertebral members V1, V2 by pedicle assemblies 12 comprising a pedicle screw 14 and a retaining cap 16. The outer surface of spinal rod 10 is grasped, clamped, or otherwise secured between the pedicle screw 14 and retaining cap 16. Other mechanisms for securing spinal rods 10 to vertebral members V1, V2 include hooks, cables, and other such devices. Examples of other types of retaining hardware include threaded caps, screws, and pins. Spinal rods 10 are also attached to plates in other configurations. Thus, the exemplary assemblies 12 shown in FIG. 1 are merely representative of one type of attachment mechanism.

The rod 10 may be constructed from a variety of surgical grade materials. These include metals such as stainless steels, cobalt-chrome, titanium, and shape memory alloys. Non-metallic rods, including polymer rods made from materials such as PEEK and UHMWPE, are also contemplated. Further, the rod 10 may be straight, curved, or comprise one or more curved portions along its length.

Figure 2:
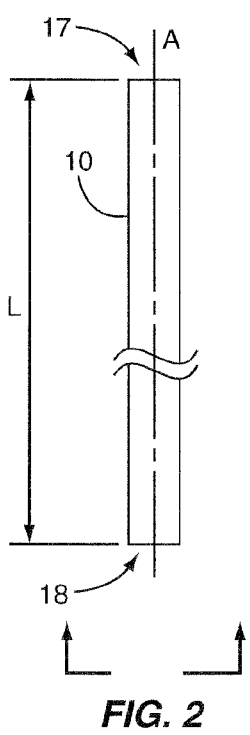
FIG. 2 is a lateral view of a spinal rod according to one or more embodiments.
Figure 3:
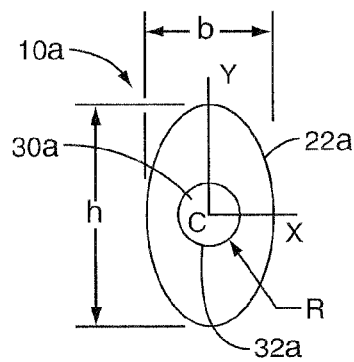

FIG. 2 shows a spinal rod 10 of the type used in the exemplary assembly 20 in FIG. 1. The rod 10 has a length between a first end 17 and a second end 18 extending along a longitudinal axis A. Other Figures described below show various embodiments of a spinal rod 10 characterized by different cross sections viewed according to the view lines illustrated in FIG. 2. For instance, FIG. 3 shows one example cross section of the spinal rod 10a. In this embodiment, the spinal rod 10a is comprised of an oval or elliptical outer surface 22a and an interior cavity or aperture 30a defined by an inner surface 32a. In one embodiment, the outer surface 22a and inner surface 32a are uniformly consistent along the entire length L of the rod 10a. That is, the cross section shown in FIG. 3 may be the same at all points along the length L of the rod 10a. The same may also be true of other cross sections described below. In one or more embodiments, the cross section of a rod 10 may vary along the length L of the rod 10.

The structural characteristics of the rod 10 may be dependent upon several factors, including the material choice and the cross section shape of the rod 10. The flexural rigidity, which is a measure of bending stiffness, is given by the equation:

$$\text{Flexural Rigidity} = E \times I \quad (1)$$

where E is the modulus of elasticity or Young's Modulus for the rod material and I is the moment of inertia of a rod cross section about the bending axis. The modulus of elasticity varies by material and reflects the relationship between stress and strain for that material. As an illustrative example, titanium alloys generally possess a modulus of elasticity in the range between about 100-120 GPa. By way of comparison, implantable grade polyetheretherketone (PEEK) possesses a modulus of elasticity in the range between about 3-4 Gpa, which, incidentally, is close to that of cortical bone.

In general, an object's moment of inertia depends on its shape and the distribution of mass within that shape. The greater the concentration of material away from the object's centroid C, the larger the moment of inertia. In FIG. 3, the moments of inertia about the x-axis $I_x$ and the y-axis $I_y$ for the area inside the elliptical outer shape 22a (ignoring the inner aperture 30a for now) may be determined according to the following equations:

$$I_x = \int y^2 dA \quad (2)$$

$$I_y = \int x^2 dA \quad (3)$$

where y is the distance between a given portion of the elliptical area and the x-axis and x is the distance between a given portion of the elliptical area and the y-axis. The intersection of the x-axis and y-axis is called the centroid C of rotation. The centroid C may be the center of mass for the shape assuming the material is uniform over the cross section. Since dimension h in FIG. 3 is larger than dimension b, it follows that the moment of inertia about the x-axis $I_x$ is larger than the moment of inertia about the y-axis $I_y$. This means that the oval shape defined by the outer surface 22a has a greater resistance to bending about the x-axis as compared to the y-axis.

The actual bending stiffness of the rod 10a shown in FIG. 3 may also depend upon the moment of inertia of the inner aperture 30a. Determining the overall flexural rigidity of the rod 10a requires an analysis of the composite shape of the rod 10a. Generally, the moment of inertia of a composite area with respect to a particular axis is the sum (or difference in the case of a void) of the moments of inertia of its parts with respect to that same axis. Thus, for the rod 10a shown in FIG. 3, the overall flexural rigidity is given by the following:

$$I_x = I_{xo} - I_{xi} \quad (4)$$

$$I_y = I_{yo} - I_{yi} \quad (5)$$

where $I_{xo}$ and $I_{xi}$ are the moments of inertia about the x-axis for the outer and inner areas, respectively. Similarly, $I_{yo}$ and $I_{yi}$ are the moments of inertia about the y-axis for the outer and inner areas, respectively.

In the present embodiment of the rod 10a shown in FIG. 3, the inner aperture 30a is symmetric about the centroid C. Consequently, the moments of inertia about the x and y axes for the area inside the outer surface 22a are reduced by the same amount according to equations (4) and (5). Still, the overall flexural rigidity of the rod 10a is greater about the x-axis as compared to the y-axis. Accordingly, a surgeon may elect to install the rod 10a in a patient to correspondingly control flexion, extension, or lateral bending. One may do so by orienting the rod 10a with the x-axis positioned perpendicular to the motion that is to be controlled. For example, a surgeon who elects to control flexion and extension may orient the rod 10a with the stiffer bending axis (x-axis in FIG. 3) approximately parallel to the coronal plane of the patient. Conversely, a surgeon who elects to control lateral bending may orient the rod 10a with the stiffer bending axis (x-axis in FIG. 3) approximately parallel to the sagittal plane of the patient. The surgeon may also elect to install the rod 10a with the x and y axes oriented at angles other than aligned with the sagittal and coronal planes of the patient.

It may be desirable to adjust the bending stiffness of the rod 10 by varying the size and shape of the inner aperture 30. For instance, a surgeon may elect to use the rods 10 disclosed herein with existing mounting hardware such as pedicle screws or hook saddles (not shown). Some exemplary rod sizes that are commercially available range between about 4-7 mm. Thus, the overall size of the rods 10 may be limited by this constraint.

Figure 4:
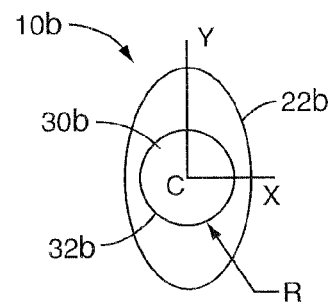

FIG. 4 shows a rod 10b similar to rod 10a (i.e., outer surface 22b is substantially similar to surface 22a) with the exception that the inner aperture 30b defined by inner surface 32b is larger than the inner aperture 30a of rod 10a. Using the equations above, one is able to determine that the overall flexural rigidity about the x and y axes is greater for rod 10a as compared to rod 10b. Rods 10a and 10b may be available as a set with a common outer surface 22a, 22b. However, since the rods have a different internal aperture 30a, 30b configuration, a surgeon may select between the rods 10a, 10b to match a desired bending stiffness.

Figure 5:
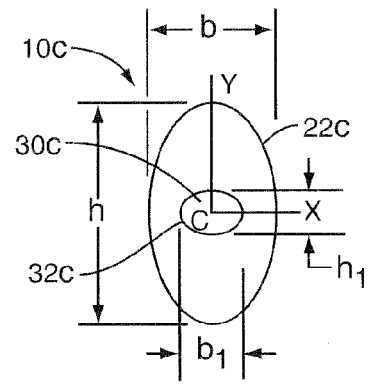

The internal aperture 30 may be asymmetric as well. For example, the rod 10c shown in FIG. 5 includes an outer surface 22c that is substantially similar to the outer surface 22a of rod 10a. However, the inner aperture 30c defined by surface 32c is elliptical or oval shaped. The inner aperture 30c has a height $h_1$ parallel to the x-axis that is less than the width $b_1$ parallel to the y-axis. That is, the moment of inertia of the inner aperture 30c is greater about the y-axis than about the x-axis. This is in contrast to the outer surface 22c, which has a larger moment of inertia about the x-axis.

Figure 6:
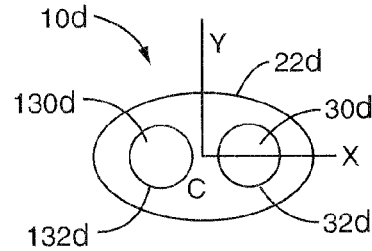

The rods 10 may also have multiple inner apertures 30. For instance, the rod 10d shown in FIG. 6 comprises a plurality of apertures 30d, 130d defined by inner surfaces 32d, 132d. The outer surface 22d may be substantially similar to the outer surface 22a of rod 10a. Notably, the exemplary apertures 30d, 130d are disposed within the interior of the rod 10d. Further, the apertures 30d, 130d are offset from the centroid C.

Figure 7:
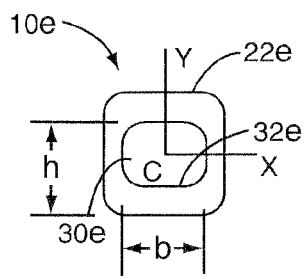

The embodiments described above have all had a substantially similar, oval shaped outer surface 22. Certainly, other shapes are possible as illustrated by the embodiment of the rod 10e shown in FIG. 7. This particular rod 10e has a square outer surface 22e that is substantially symmetric relative to axes X and Y. However, the inner aperture 30e defined by inner surface 32e is asymmetric relative to these same X and Y axes. Inner surface 32e is substantially rectangular and defined by dimensions b and h. Specifically, dimension b (parallel to the Y-axis) is not equal to dimension h (parallel to the X-axis). In the embodiment shown, dimension b is larger than dimension h. Therefore, the aperture 30e has a larger moment of inertia relative to the Y-axis as compared to the X-axis. Consequently, according to equations (4) and (5), the rod 10e has a greater bending strength about the X-axis as compared to the Y-axis.

Figure 8:
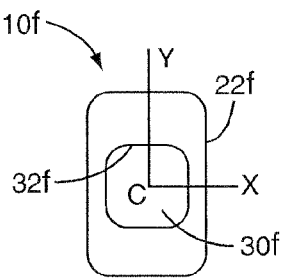
Figure 9:
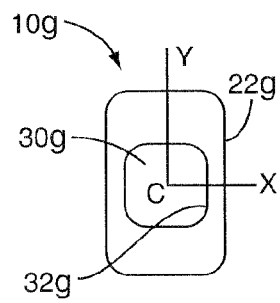

The rod 10f shown in FIG. 8 has rectilinear inner 32f and outer 22f surfaces. However, in contrast to rod 10e, the inner surface 32f is substantially square and outer surface 22f is substantially rectangular. This configuration is analogous to rod 10a shown in FIG. 3 in that the inner aperture 30f is symmetric about the X and Y axes while the outer surface 22f is asymmetric about the X and Y axes. The rod 10g shown in FIG. 9 has both an inner aperture 30g and an outer surface 22g that are asymmetric about the X and Y axes. The same is true of the rod 10c shown in FIG. 5. However, rod 10g has an inner aperture 30g and an area inside the outer surface 22g that have larger moments of inertia about the same X-axis. This is due, in part, to the fact that the rectangular inner aperture 30g and outer surface 22g are substantially aligned.

Figure 10:
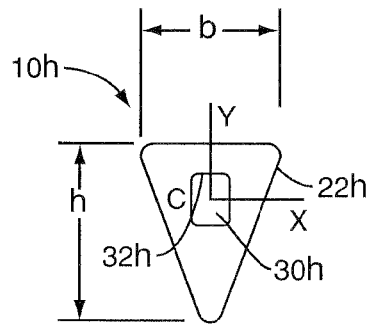
Figure 11:
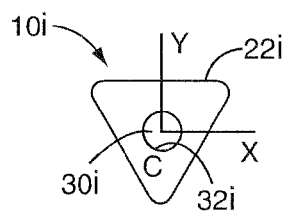
Figure 12:
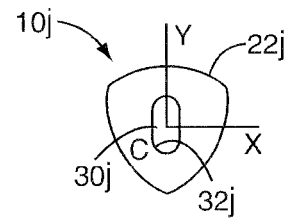

The rod 10 may also have substantially triangular outer surfaces 22 as evidenced by the embodiments 10h, 10i, and 10j. In FIG. 10, the outer surface 22h is shown as an isosceles triangle that has a larger height h (parallel to the X-axis) than base b (parallel to the Y-axis). This may tend to yield a rod 10h having a greater moment of inertia about the X-axis. By comparison, the rod 10i shown in FIG. 11 comprises a triangular outer surface 22i that is substantially equilateral. The rod 10j shown in FIG. 12 comprises a substantially triangular outer surface 22j that is substantially equilateral, albeit with non-linear sides. The inner apertures 30h, 30i, 30j may be shaped as shown in FIGS. 10-12 or as desired in accordance with the discussion provided above.

Figure 13:
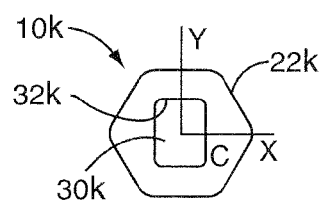
Figure 14:
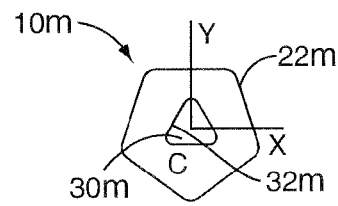

Other rods 10 may have polygonal shapes such as the embodiments illustrated in FIGS. 13 and 14. The rod 10k shown in FIG. 13 comprises a hexagonal outer surface 22k while rod 10m in FIG. 14 comprises a pentagonal outer surface 22m. The rods 10 may have more sides if desired.

Figure 15:
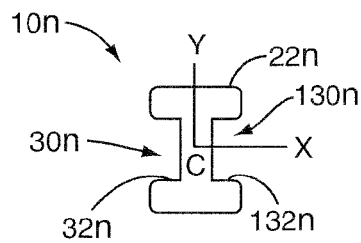
Figure 16:
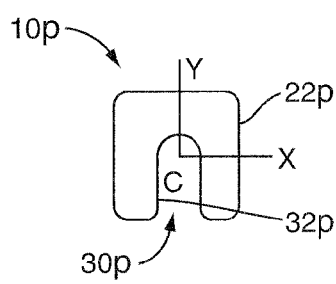

The embodiments described thus far have included an aperture 30 that is substantially contained within the interior of the outer surface 22. In other embodiments, the aperture 30 may intersect with the outer surface 22. This can be seen in the exemplary embodiments shown in FIGS. 15 and 16. In FIG. 15, the rod 10n comprises two apertures 30n, 130n that are defined by inner surfaces 32n, 132n. As indicated, the inner surfaces 32n, 132n intersect the outer surface 22n resulting in open apertures 30n, 130n. The rod 10n is shaped similar to an I-beam that has a greater moment of inertia and bending stiffness about the X-axis. By way of comparison, the rod 10p shown in FIG. 16 also has a single open aperture 30p defined by an inner surface 32p that intersects with the outer surface 22p.

The rods 10 may also have a substantially circular outer surface 22 similar to many conventional rods, thus accommodating existing rod securing hardware (not shown). This is illustrated by the exemplary rods 10q, 10r, and 10s shown in FIGS. 17, 18, and 19. In each case, the outer surface 22q-s of the rod 10q-s is substantially circular and/or characterized by a substantially constant radius. As such, the moment of inertia about axes X and Y is substantially the same for the areas within the outer surface 22q-s. However, the moment of inertia about the X and Y axes for the rod 10q-s may be altered by including an asymmetric inner aperture 30q-s.

In FIG. 17, the inner aperture 30q defined by inner surface 32q has a larger moment of inertia about the X-axis. Thus, the rod 10q has a larger moment of inertia about the Y-axis (pursuant to equations (4) and (5)). In FIG. 18, the inner aperture 30r defined by inner surface 32r is also substantially circular. However, the inner aperture 30r is offset from centroid C. Further, the inner surface 32r is tangent to the Y-axis, but spaced away from the X-axis. Thus, the moment of inertia of the inner aperture 30r is larger with respect to the X-axis as compared to the Y-axis. Consequently, the moment of inertia and bending stiffness of the overall rod 10r is larger about the Y-axis.

FIG. 19 shows another embodiment of a rod 10s having an open inner aperture 30s. In this embodiment, the inner surface 32s has a substantially constant radius and intersects the substantially circular outer surface 22s. The inner aperture 30s is offset from the centroid C, but aligned with the Y-axis in the orientation shown. Therefore, the inner aperture 30s has a larger moment of inertia about the X-axis. The bending stiffness of the overall rod 10s is therefore greater about the Y-axis.

FIG. 20 shows the same rod 10q as illustrated in FIG. 17. In this particular view, the rod 10q comprises a first set of markings 34 (the – sign in the embodiment shown) and a second set of markings 36 (the + sign in the embodiment shown). The markings 34, 36 may be stamped, engraved, or otherwise included on the rod as an indication of the bending stiffness in the direction of the marking. The markings 34, 36 may be included on an end 17, 18 of the rod 10q as shown or on the outer surface 22q.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For example, embodiments described above have contemplated one or two inner apertures 30 to modify the moments of inertia about one axis relative to another. The rods 10 do not need to be limited to this number of apertures. The moment of inertia equations provided herein allow one to calculate moments of inertia for any number of apertures and flexural rigidity of the overall rod 10. The present embodiments are, therefore, to be considered in all respects as illustrative and not restrictive, and all changes coming within the meaning and equivalency range of the appended claims are intended to be embraced therein.

What is claimed is:

1. A vertebral rod for stabilizing a patient's spine comprising:
   a solid elongated body with first and second ends and having an elongated cross-sectional shape with a major axis and a minor axis and a centroid positioned at an intersection of the axes;

first and second longitudinal channels that are spaced apart and are each contained within and extend through the body, each of the channels being positioned on the major axis and being spaced away from the centroid;

the rods and the channels being symmetrical about the major and minor axis;

the body being limited to just the first and second longitudinal channels with a remainder of the body being channel-free, the channels each being unobstructed;

the body having a first flexural rigidity along the major axis and a different second flexural rigidity along the minor axis.

2. The vertebral rod of claim 1, wherein the body includes an elliptical cross-sectional shape and each of the channels includes a circular cross-sectional shape.

3. The vertebral rod of claim 2, wherein the channels are positioned on opposing sides of the centroid.

4. The vertebral rod of claim 3, where the channels have the same cross-sectional size.

5. The vertebral rod of claim 1, wherein the body is constructed of a non-metallic material.

6. The vertebral rod of claim 1, wherein the major axis is perpendicular to the minor axis.

7. The vertebral rod of claim 1, wherein each of the channels is positioned an equal distance away from the centroid along the major axis.

8. A vertebral rod for stabilizing a patient's spine comprising:

an elongated body with an elliptical cross-sectional shape having a major axis and a minor axis;

the body consisting of first and second longitudinal channels that extend along a length of the body, the channels being positioned on and spaced apart along the major axis and contained within an interior of the body, the channels each being unobstructed;

the rods and the channels being symmetrical about the major and minor axis;

the body having a first flexural rigidity along the major axis and a different second flexural rigidity along the minor axis.

9. The vertebral rod of claim 8, wherein the major and minor axes intersect at a centroid and each of the channels is spaced away from the centroid.

10. The vertebral rod of claim 9, wherein the channels are positioned on opposing sides of the centroid.

11. The vertebral rod of claim 10, wherein a distance between the channels is less than a diameter of either of the channels.

12. The vertebral rod of claim 8, wherein the body has an elliptical cross-sectional shape and each of the channels includes a circular cross-sectional shape.

13. The vertebral rod of claim 8, wherein the body is constructed of a non-metallic material.

14. The vertebral rod of claim 8, wherein the major axis is perpendicular to the minor axis.

15. A vertebral rod for stabilizing a patient's spine, the rod comprising:

an elongated body with first and second ends and having an elliptical cross-sectional shape with a major axis and a minor axis and a centroid positioned at an intersection of the axes, the major axis being perpendicular to the minor axis;

first and second longitudinal channels that each have circular cross-sectional shapes and are spaced apart on the major axis, each of the channels is contained within and extends through the body, each of the channels is spaced away from the centroid, the channels each being hollow and unobstructed;

the rods and the channels being symmetrical about the major and minor axis;

the body being limited to just the first and second longitudinal channels;

the body having a first flexural rigidity along the major axis and a different second flexural rigidity along the minor axis.

16. The vertebral rod of claim 15, wherein a distance between the channels is less than a diameter of either of the channels.

17. The vertebral rod of claim 15, wherein the channels have the same cross-sectional size.

18. The vertebral rod of claim 15, wherein the rod is constructed of a non-metallic material.

\* \* \* \* \*